United States Patent [19]
Kesling

[11] 3,990,151
[45] Nov. 9, 1976

[54] ADJUSTABLE ORTHODONTIC BAND
[76] Inventor: Peter C. Kesling, Green Acres, LaPorte, Ind. 46350
[22] Filed: Apr. 14, 1975
[21] Appl. No.: 567,550

[52] U.S. Cl. ................................. 32/14 A
[51] Int. Cl.² .................................. A61C 7/00
[58] Field of Search ............ 32/14 A, 63; 63/15.5; 24/20 R, 115 A, 129 W

[56] References Cited
UNITED STATES PATENTS
1,173,998  2/1916  Depew ............................... 32/14 A
1,670,361  5/1928  Johnson ............................ 32/14 A
2,790,238  4/1957  Trangmar ............................. 32/63

FOREIGN PATENTS OR APPLICATIONS
1,408,730  11/1965  France ............................... 63/15.5

*Primary Examiner*—Louis G. Mancene
*Assistant Examiner*—Jack Q. Lever
*Attorney, Agent, or Firm*—Lockwood, Dewey, Zickert & Alex

[57] ABSTRACT

An adjustable metal orthodontic band, including a sleeve-shaped body having folds, pleats or corrugations which permit expansion so that the band may fit teeth of various size.

21 Claims, 9 Drawing Figures

ADJUSTABLE ORTHODONTIC BAND

This invention relates in general to orthodontic bands, and more particularly to adjustable metal orthodontic bands wherein one band size will fit teeth of various size within a range.

Mounting of orthodontic appliances on teeth is principally accomplished by use of metal bands which engage the buccal or labial, lingual, mesial and distal sides of the teeth. Appliances are suitably attached to the bands and the bands are then cemented in place on the teeth.

One of the preferred band structures used today is in the form of a sleeve-shaped seamless band. The term "seamless" includes a band having no visible seam as well as a band where two edges of material are brought together and secured such as by welding or the like. Further, such seamless bands are usually preformed where they would include the height of contour formation, but they can be provided without same. Because of the various sizes of teeth encountered in patients, utilization of the seamless band demands that a high number of sizes be made available depending upon the manufacturer. Upwards of 200 or more different sizes are necessary to effectively utilize this banding. For example, there are usually thirty different sizes for the maxillary centrals, thirty different sizes for the maxillary laterals, eighteen different sizes for the maxillary cuspids, 32 different sizes for the maxillary bicuspids, and 32 different sizes for the maxillary molars. Accordingly, for the maxillaries alone, there are provided 132 sizes. Many sizes are also needed for the mandibular teeth. Orthodontists who prefer use of seamless bands therefore must inventory a large number of band sizes and maintain close control over the inventory.

The present invention overcomes the above objectionable inventory problem of so many different sizes in that the invention relates to an adjustable seamless band which will reduce the number of sizes needed by more than half. The band of the invention may be preformed with the height of contour formation or without same. For example, for the maxillary centrals, the band of the present invention enables stocking of about twelve band sizes that will satisfy the thirty band sizes heretofore needed. Thus, the present invention will simplify and make more efficient the band inventory problem of an orthordontist.

Heretofore, it has been known to provide adjustable bands, such as one having a split body configuration with a tightening and loosening mechanism, such as a nut and bolt assembly. This adjustable band is objectionable from the standpoint it leaves an excessive amount of mechanism in the mouth that is bothersome to the patient and also because it is difficult to handle. There also have been heretofore known loop bands that in the first instance are in the form of a seamless band, where a part of the band is looped outside of the band body that engages the teeth to be squeezed together, soldered and then have the excess cut off. The soldering and cutting operations complicate the mounting procedure. It has also been known to cement a wire around a tooth to act as a band, but such makes it difficult for the attachement of applicances. It has further been known to shape preformed molar bands with buccal and/or lingual cusp indents adjacent the occlusal edge to provide a more accurate anatomical fit. But such indents are not intended to allow expansion for fitting teeth of various sizes. These indents are only located at the occlusal portion of bands and cannot allow expansion to fit teeth of various sizes because it is the gingival portion of the bands which must pass over the largest circumference of the teeth, not the occlusal. It may be further appreciated that mounting a band on a tooth requires the leading or gingival edge to first engage the tooth. Accordingly, in order that a band be adjustable, expansion must be available in the leading portion of the band.

Accordingly, it is an object of the present invention to obviate the above difficulties and provide an adjustable metal orthodontic band for mounting orthodontic appliances to teeth.

A further object of this invention is in the provision of an adjustable orthodontic band which may be preformed and seamless and adjustable for being mounted on various sizes of teeth within a range.

A still further object of this invention resides in the provision of an adjustable orthodontic band having a seamless body with folds, pleats or corrugations formed to enable the body to be suitably adjusted for fitting on teeth of various size within a range.

Another object of this invention is in the provision of a seamless orthodontic band that is adjustable to fit teeth of various size and which has reinforced side walls to enable the band to be driven into place on a tooth with less chance of incurring damage and the need of replacement.

Another object of the invention is to provide orthodontic bands with areas having varying degrees of hardness and flexibility to permit a greater adjustability in one area than another, wherein the degrees of hardness and flexibility are obtained by localized heat treating and/or formation of pleats or folds.

Other objects, features and advantages of the invention will be apparent from the following detailed disclosure, taken in conjunction with the accompanying sheets of drawings, wherein like reference numerals refer to like parts, in which.

Figure 1:
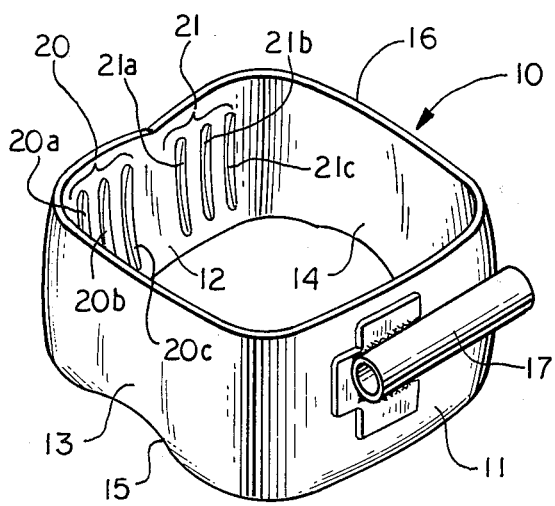
FIG. 1 is a perspective view of a band constructed according to the invention.
Figure 3:
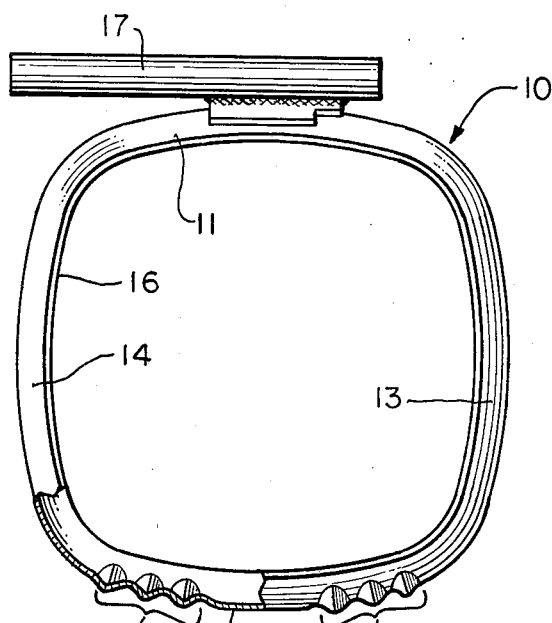
FIG. 3 is a top plan view of the band of FIG. 2 and also a cut-away taken substantially along line 3—3 of FIG. 2.
Figure 2:
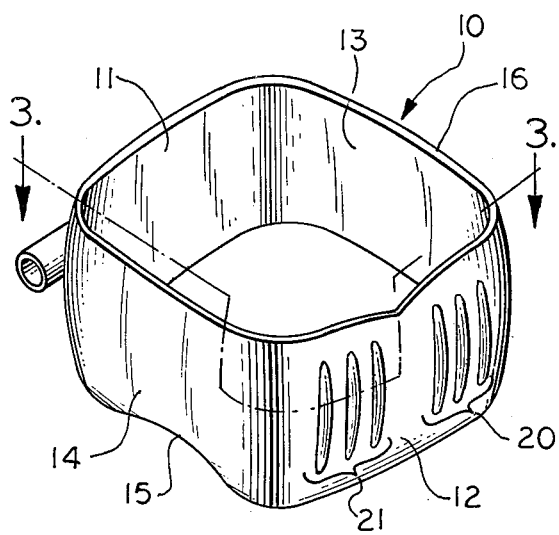
FIG. 2 is a perspective view of the band in FIG. 1 looking at it from the opposite direction.

Referring now to the drawings, and particularly to the embodiment of FIGS. 1 to 3, a band 10 is shown embodying the invention and which includes a labial or buccal wall 11, a lingual wall 12 opposed to the buccal wall 11, a mesial wall 13 and a distal wall 14, all of which walls have a common gingival edge 15 and a common occlusal edge 16. Accordingly, the walls extend occlusogingivally in relation to a tooth. The particular band 10 is one suitable for application to molar teeth, and accordingly a buccal tube appliance 17 is suitably secured to the outer side of the buccal wall 11, so that it may anchor in archwire. However, the present invention is not restricted to molar bands, as is evident by the other embodiments illustrated. Any type of appliance may be secured to the outer side of the buccal wall or the outer side of the lingual wall, as needed in the particular case of the patient, and depending upon which molar the band is mounted on. The band is constructed of metal and preferably of a type suitable for the mouth of the patient, such as a stainless steel type. Further, it can be observed that the buccal, lingual, mesial and distal walls are interconnected together at their ends to form a seamless band. Essentially, it is seen the band illustrated and the bands of the type concerned here are generally of the preformed metal seamless type where the height of contour formation is embodied in the band. It is understood a band of this type is adapted to be suitably secured to a tooth, such as by a cement.

In accordance with the invention, the band 10 is adjustable by means of pleats, folds or corrugations formed in one of the walls. In the embodiment of FIGS. 1 to 3, first and second sets of corrugations 20 and 21 are formed in the lingual wall 12. These sets of corrugations include respectively corrugations 20a, 20b and 20c, and corrugations 21a, 21b and 21c. The corrugations extend oclusogingivally between the gingival and occlusal edges of the lingual wall. Further, the corrugations terminate short of the gingival and occlusal edges of the wall and therefore extend intermediate the wall and over the height of contour portion of the band which is the central area between the occlusal and gingival edges. While two sets of corrugations are illustrated in the embodiment of FIGS. 1 to 3, it can be appreciated that any number of sets of corrugations could be provided in the lingual wall or in the lingual wall and/or any of the other walls of the band. Further, while only three corrugations are shown for each set of corrugations, it can be appreciated that one or more corrugations may be provided in each set. Inasmuch as the corrugations extend occlusgingivally, they provide a certain reinforcing to the lingual wall and render it stronger than the other walls. The corrugations provide an adjustability feature to the band, wherein the band may be used on a tooth of a size that it is formed as shown in FIGS. 1 to 3, or in the event that the tooth has a larger size, the band may be increased in size as needed by expansion of the corrugations so that it will fit teeth of various sizes. The lingual wall is in this case the expansion wall inasmuch as the corrugations are only provided in this wall, and it can be appreciated that the mesiodistal length of the wall may be increased by either reducing the depth of one or more of the corrugations between the beaks of a pliers or with other suitable tools prior to the mounting of the band onto a tooth, or by forcibly mounting the band on a tooth causing expansion. If the band is increased in size during the mounting of same on a tooth, it will automatically expand and conform snugly to the size of the tooth as needed. Once the band is on the tooth, it can be appreciated that the corrugations 20 and 21 would not produce any undue sharp edges within the mouth that would injure the tongue. While the occlusogingivally extending corrugations are illustrated herein as extendinng perpendicular to the band edges, it should be appreciated they may be somewhat inclined to the edges and still function to properly provide band expansion. Further, it may be desirous to form the corrugations around attachments on the band.

In order to enhance the flexibility of the corrugations to render them more easily expansible, any part or all of them and flat areas of the band between, gingival and/or incisal to the corrugations, may be annealed by well known annealing methods. Of course, this applies to any of the embodiments in the present application. It can now be appreciated tht the adjustable seamless band of the invention will enable the fitting of a single band onto teeth of various sizes and shapes within a range which would overall decrease the number of sizes of ordinary bands needed for handling all sizes of teeth.

Figure 4:
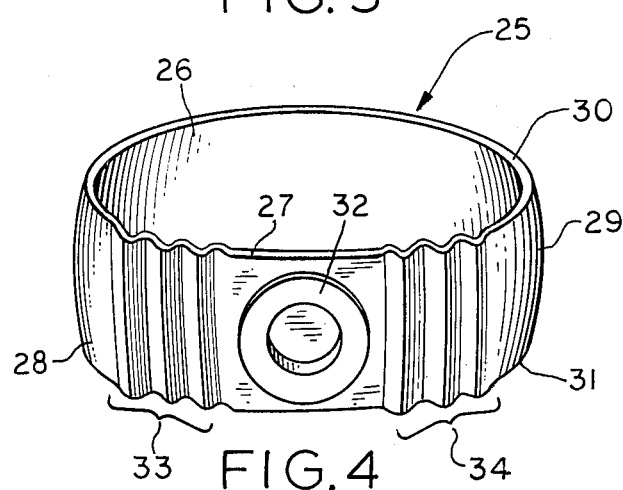
FIG. 4 is a perspective view of a modified band according to the invention.

The embodiment of FIG. 4 differs primarily from the embodiment of FIGS. 1 to 3 in the manner in which the corrugations are formed in the wall of the band. The shape of the band differs to illustrate the use of the present invention in connection with bands for teeth other than molar teeth, and the band of FIG. 4 would be suitable for use on bicuspid teeth. This band is generally designated by the numeral 25 and includes a labial or buccal wall 26, a lingual wall 27, and mesial and distal walls 28 and 29. Each of the walls is defined as terminating at the occlusal edge 30 and the gingival edge 31. A lingual button appliance 32 is suitably secured to the lingual wall 27. It can be appreciated that a bracket may be secured to the outer side of the buccal wall 26 if so desired. Further, it is not necessary to have a lingual button on the lingual wall, and this is optional depending on the need. First and second sets of corrugations 33 and 34 are provided in the lingual wall at the opposite sides of the lingual button 32 for giving the band the ability to expand for handling various sizes of teeth. The corrugations extend through the occlusal and gingival edges in contrast to the corrugations in the embodiments of FIGS. 1 to 3, which terminate short of the edges. Accordingly, it can be appreciated here that the corrugations provide rigidity or reinforcement to the wall in which they are located and also provide adjustability to the bands. Again, the corrugations extend occlusogingivally, and the use of a driving tool on the corrugations would reduce the possibility of damaging of the band when it is driven onto a tooth. As above mentioned, the band may also be enlarged by flattening one or more of the corrugations. For example, depending on the size of the corrugations, the flattening of one corrugation could increase the circumference of a band approximately .010 inch.

Figure 5:
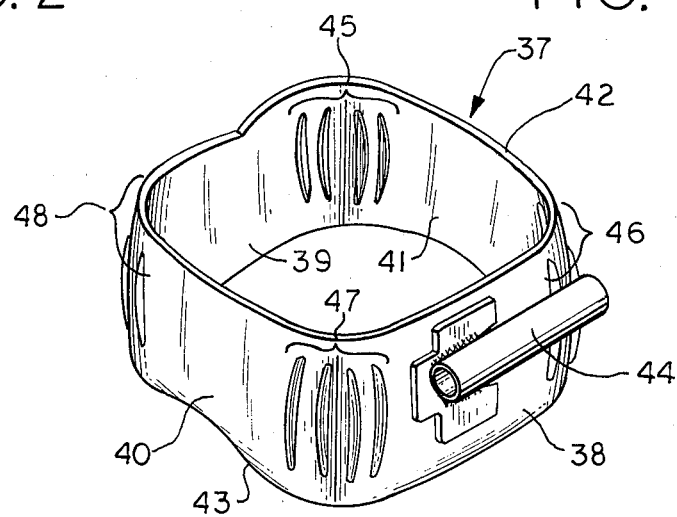
FIG. 5 is a perspective view of a still further modified band according to the invention.

The embodiment of FIG. 5 differs from the previous embodiment in providing the corrugations at the four corners of a molar band. The band in FIG. 5 is generally designated by the numeral 37 and includes buccal wall 38, a lingual wall 39 and mesial and distal walls 40 and 41. The walls extend from the occlusal edge 42 to the gingival edge 43. A buccal tube appliance 44 is suitably secured to the buccal wall 38. In this embodiment, the corrugations are provided in four sets 45, 46, 47 and 48, all located at the corners of the band. While it is illustrated that four corrugations are provided in each set, it should be appreciated that any number of corrugations may be included in a set. Again, the corrugations terminate short of the occlusal and gingival edges as in the embodiment of FIGS. 1 to 3, and therefore this embodiment differs primarily in the location and the number of sets of corrugations for the band. It can be appreciated that the larger number of sets of corrugations would provide even greater expansion of the band so that it would fit on a larger number of teeth of different sizes.

Figure 6:
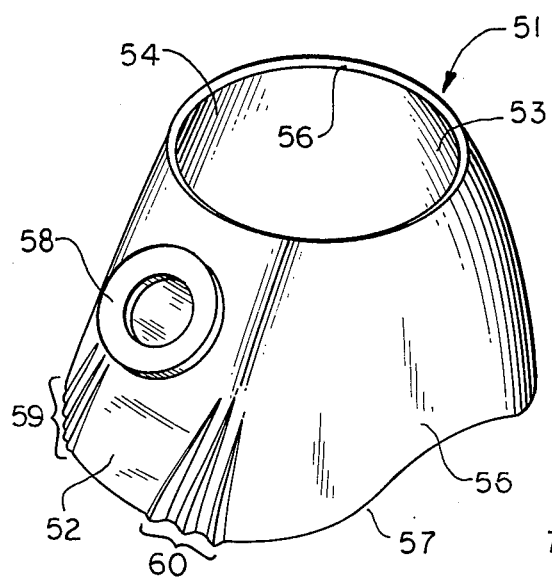
FIG. 6 is a perspective view of a further modification of the invention.

The embodiment of FIG. 6 illustrates a band 51 that is of the type that may be used on the cuspids, and which includes a lingual wall 52, a labial wall 53, and mesial and distal walls 54 and 55. The walls have a common occlusal edge 56 and a common gingival edge 57. The band 51 is illustrated as having a lingual button appliance 58 mounted on the lingual wall 52, although it can be appreciated that any desired type of appliance may be mounted on this band. It can also be appreciated that a bracket of some sort can be mounted on the labial wall. This embodiment differs primarily in that the corrugations are provided adjacent one edge of the band. In this embodiment, first and second sets of corrugations 59 and 60 are provided at the gingival edge of the band. Each set of corrugations here is positioned generally at the juncture of the lingual wall with the mesial and distal walls, although it can be appreciated that they may be placed at any suitable location around the band. The corrugations extend through the gingival edge and to a point short of the half-way distance between the gingival and occlusal edge. However, it can be appreciated that the distance the corrugations terminate may vary according to the need of expansion. Most generally, th expansion needed or differences in sizes of cuspid teeth are experienced at the gingival area of the tooth, and accordingly the corrugations here are placed in that area.

Figure 7:
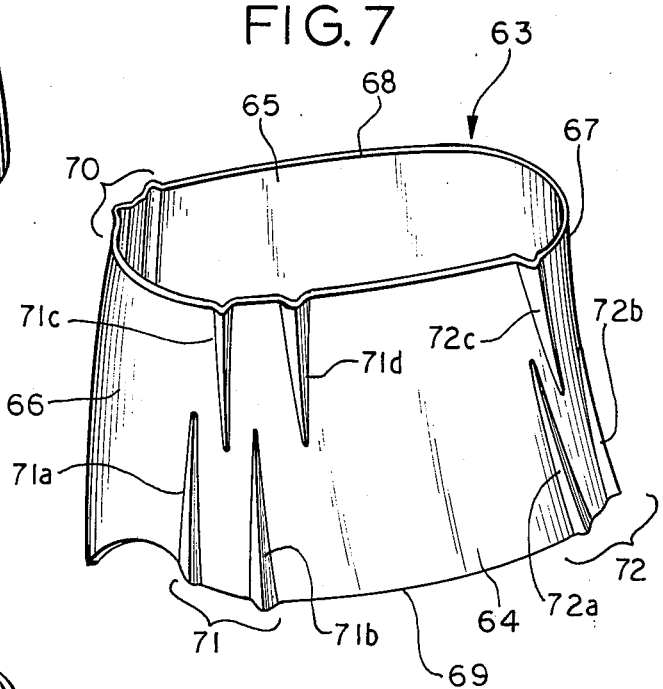
FIG. 7 is a perspective view of a still further modification of the invention.

Another embodiment is shown in FIG. 7, wherein the band 63 includes a lingual wall 64, a labial wall 65, and mesial and distal walls 66 and 67, having a common occlusal edge 68 and a common gingival edge 69. Three sets of corrugations 70, 71 and 72 are provided. The set of corrugations 70 is located generally at the juncture of the labial wall 65 and the mesial wall 66, while the sets of corrugations 71 and 72 are generally located at the juncture of lingual wall 64 and the mesial and distal walls 66 and 67. However, the location of these sets of corrugations may vary along any part of the walls, but it is preferred that they be at least in an area where they will not interfere with other movements of teeth and where they best provide the expansion characteristics of the band as needed for handling various sizes and shapes of teeth. The sets of corrugations 71 and 72 best illustrate this embodiment, wherein the set 71 includes corrugations 71a and 71b which extend from the gingival edge 69 to a point near the center between the occlusal and gingival edges, while the corrugations 71c and 71d extend from the occlusal edge toward the corrugations 71a and 71b, but in staggered relation thereto and to a point substantially at the center point between the occlusal and gingival edges of the band. The set of corrugations 72 differs slightly in that it is provided with corrugations 72a and 72b extending from the gingival edge and a single corrugation 72c extending from the occlusal edge. It can be seen that the depth of the corrugations is the greatest at the occlusal or gingival edge and then tapers to no depth at all where it terminates intermediate the walls of the band.

Figure 8:
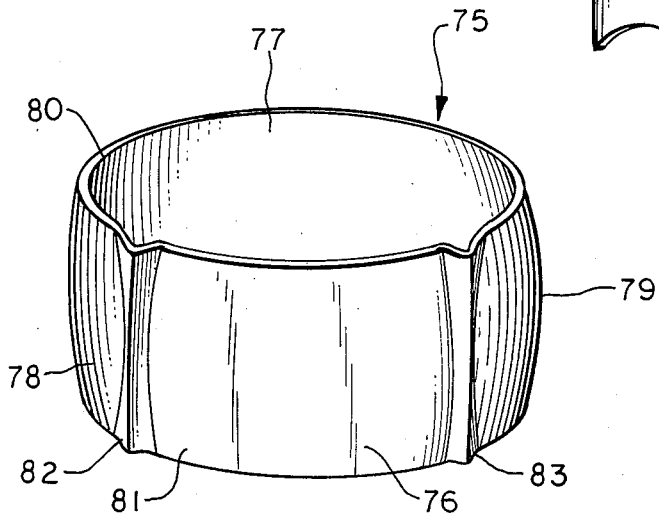
FIG. 8 is a perspective view of a band that constitutes a still further modification of the invention.

The embodiment of FIG. 8 differs from the other embodiments in that it shows a band 75 having a lingual wall 76, a labial wall 77 and mesial and distal walls 78 and 79. The walls have a common occlusal edge 80 and a common gingival edge 81. This embodiment differs in that the corrugations are non-uniform in depth throughout their length and wherein a corrugation 82 and a corrugation 83 provide the necessary expansion range for the band to handle various sizes of teeth. It can be seen that the corrugations extend through the occlusal and gingival edges and that their depth is greater at the occlusal and gingival edges than at the center point, which is between the edges, and it is here seen that the expected expansion of the band would be greater at the occlusal and gingival edges than at the center point. This band would be useful for a bicuspid, although it should be appreciated that this type of corrugation could be provided in any of the bands used.

Figure 9:
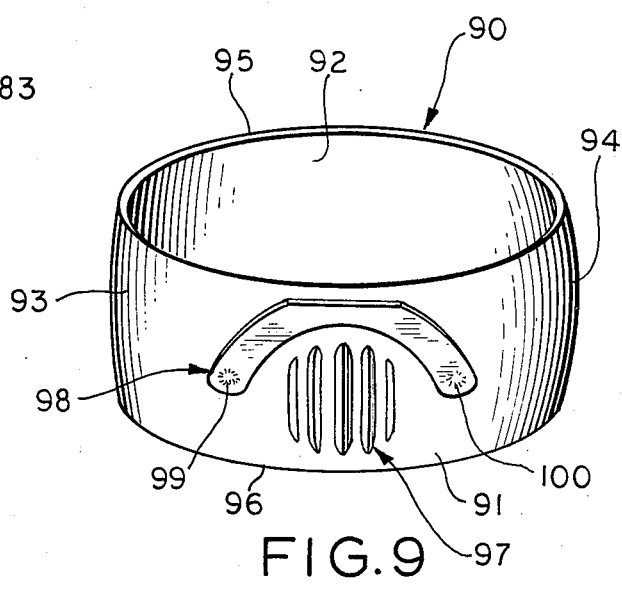
FIG. 9 is a perspective view of a band illustrating a further modification of the invention.

A further embodiment of the invention is shown in FIG. 9, which differs from the other embodiments primarily in the manner in which the pleats, folds or corrugations are formed in the band. The band here is generally designated by the numeral 90 annd is in the general form of the band shown in FIG. 8 in that it includes a lingual wall 91, a labial wall 92, and mesial and distal walls 93 and 94. The walls have a common occlusal edge 95 and a common gingival edge 96. A single set of corrugations 97 is formed on the lingual wall 91 intermediate the occlusal and gingival edges of the band. To generally assist in the placement of the band onto a tooth, a lingual cleat 98 is also positioned on the lingual wall 91. This cleat is horseshoe-shaped and suitably secured to the lingual wall such as by welding or the like at its ends 99 and 100. As illustrated in FIG. 9, the cleat generally surrounds on three sides the set of corrugations 97 and therefore defines a bridge between the points of attachment at their ends 99 and 100. It will be understood the cleat lies adjacent the outer surface of the lingual wall 91. Further, the cleat is made of a suitable material, such as spring or soft steel, so that the terminal ends 99 and 100 will spread apart causing the expansion of the corrugations 97 when driving the band onto a tooth. This form of the invention is useful where the orthodontist would want a cleat mounted on the band to assist in mounting the band on a tooth. It can be appreciated that the cleat here is not secured to the band except at its ends 99 and 100.

From the foregoing, it can be appreciated that the present invention resides in the provision of pleats, folds or corrugations in the walls of a band which is seamless so that it can be easily expanded to fit teeth of various sizes, and wherein the overall number of bands needed for inventory can be substantially reduced from the type of seamless bands heretofore known which are not adjustable, while still achieving the desired band fit. While the band of the invention is made of metal, such as a stainless steel, it should be appreciated it could be made of any other suitable material that would be corrugated and which would allow expansion like a metal band.

It will be understood that modifications and variations may be effected without departing from the scope of the novel concepts of the present invention, but it is understood that this application is to be limited only by the scope of the appended claims.

The invention is hereby claimed as follows:

1. An adjustable metal orthodontic band for mounting orthodontic appliances on the tooth of an orthodontic patient comprising, a sleeve-shaped seamless body, said body having walls adapted to engage buccal, lingual, mesial and distal surfaces of a tooth, and means on at least one wall including a plurality of occlusogingivally extending corrugations formed in the body prior to fitting permitting expansion of the band to enlarge same in at least the gingival portion thereof to enable fitting teeth of various sizes.

2. An adjustable metal orthodontic band as defined in claim 1, wherein said corrugations extend from the occlusal edge to the gingival edge of the body.

3. An adjustable metal orthodontic band as defined in claim 1, wherein said corrugations are provided on a plurality of walls of the body.

4. An adjustable metal orthodonic band as defined in claim 1, wherein said corrugations are provided on the lingual wall of the body.

5. An adjustable metal orthodontic band as defined in claim 1, wherein said corrugations are uniform in depth along their length.

6. An adjustable metal orthodontic band as defined in claim 1, wherein said corrugations are provided on the lingual and buccal walls of the body.

7. An adjustable metal orthodontic band as defined in claim 1, wherein said corrugations are grouped together.

8. An adjustable metal orthodontic band as defined in claim 1, wherein at least part of the corrugations are annealed.

9. An adjustable metal orthodontic band as defined in claim 1, wherein the corrugations are annealed.

10. An adjustable metal orthodontic band as defined in claim 1, wherein a plurality of sets of corrugations are provided.

11. An adjustable metal orthodontic band as defined in claim, wherein a set of corrugations is positioned on the lingual wall, and a horseshoe-shaped lingual cleat substantially surrounding the set of corrugations on three sides and secured to the band at its ends on the mesial and distal sides of the set.

12. A preformed adjustable metal orthodontic band for mounting orthodontic appliances on the tooth of an orthodontic patient comprising, a sleeve-shaped seamless body, said body having connecting walls, and means on at least one wall permitting expansion of the band to enlarge same to enable fitting teeth of various sizes, said means including a plurality of occlusogingival extending corrugations.

13. A preformed adjustable metal orthodontic band as defined in claim 12, wherein said means includes a plurality of sets of occlusogingival extending corrugations.

14. An adjustable metal orthodontic band for mounting orthodontic appliances on the tooth of an orthodontic patient comprising, a sleeve-shaped body, said body having walls adapted to engage buccal, lingual, mesial and distal surfaces of a tooth, and means on at least one wall including a plurality of occlusogingivally extending corrugations formed in the body permitting expansion of the band in at least the gingival portion thereof to enable fitting teeth of various sizes, said corrugations terminating short of the occlusal and gingival edges of the body.

15. An adjustable metal orthodontic band for mounting orthodontic appliances on the tooth of an orthodontic patient comprising, a sleeve-shaped body, said body having walls adapted to engage buccal, lingual, mesial and distal surfaces of a tooth, and means on at least one wall including a plurality of occlusogingivally extending corrugations formed in the body permitting expansion of the band in at least the gingival portion thereof to enable fitting teeth of various sizes, said corrugations extending from the occlusal edge of the body to a point intermediate the occlusal and gingival edges thereof.

16. An adjustable metal orthodontic band for mountinng orthodontic appliances on the tooth of an orthodontic patient comprising, a sleeve-shaped body, said body having walls adapted to engage buccal, lingual, mesial and distal surfaces of a tooth, and means on at least one wall including a plurality of occlusogingivally extending corrugations formed in the body permitting expansion of the band in at least the gingival portion thereof to enable fitting teeth of various sizes, said corrugations extending from the gingival edge of the body to a point intermediate the occlusal and gingival edges thereof.

17. An adjustable metal orthodontic band for mounting orthodontic appliances on the tooth of an orthodontic patient comprising, a sleeve-shaped body, said body having walls adapted to engage buccal, lingual, mesial and distal surfaces of a tooth, and means on at least one wall including a plurality of occlusogingivally extending corrugations formed in the body permitting expansion of the band in at least the gingival portion thereof to enable fitting teeth of various sizes, said corrugations extending from both the occlusal and gingival edges of the body to pints intermediate the occlusal and gingival edges thereof.

18. An adjustable metal orthodontic band as defined in claim 17, wherein the corrugations overlap at said points.

19. An adjustable metal orthodontic band for mounting orthodontic appliances on the tooth of an orthodontic patient comprising, a sleeve-shaped body, said body having walls adapted to engage buccal, lingual, mesial and distal surfaces of a tooth, and means on at least one wall including at least one occlusogingivally extending corrugation formed in the body permitting expansion of the band in at least the gingival portion thereof to enable fitting teeth of various sizes, said corrugation being non-uniform in depth along its length.

20. An adjustable metal orthodontic band for mounting orthodontic appliances on the tooth of an orthodontic patient comprising, a sleeve-shaped body, said body having walls adapted to engage buccal, lingual, mesial and distal surfaces of a tooth, and means on at least one wall including a plurality of occlusogingivally extending corrugations formed in the body permitting expansion of the band in at least the gingival thereof to enable fitting teeth of various sizes, and at least a part of the flat area between adjacent corrugations or at the gingival and/or occlusal ends of the corrugations is softer than the remaining parts of the band.

21. An adjustable metal orthodontic band for mounting orthodontic appliances on the tooth of an orthodontic patient comprising, a sleeve-shaped seamless body, said body having connecting walls adapted to engage buccal, lingual, mesial and distal surfaces of a tooth, said walls having common occlusal and gingival edges, and occlusogingivally extending corrugation means formed on the body prior to fitting that permits expansion of the band to enlarge same in at least the gingival portion thereof to enable fitting teeth of various sizes, said corrugation means defining a plurality of formations along a plane extending through the walls of the body and through said means and between the edges.

* * * * *

UNITED STATES PATENT AND TRADEMARK OFFICE
CERTIFICATE OF CORRECTION

PATENT NO. : 3,990,151
DATED : November 9, 1976
INVENTOR(S) : Peter C. Kesling

It is certified that error appears in the above-identified patent and that said Letters Patent are hereby corrected as shown below:

```
Col. 1, line 64, change "applicances" to --appliances--;
Col. 3, line 42, change "occlusgingivally" to
                        --occlusogingivally--;
        line 66, change "extendinng" to --extending--;
Col. 4, line 9,  change "tht" to --that--;
Col. 5, line 26, change "th" to --the--;
Col. 6, line 52, change "would" to --could--;
Col. 7, line 30, after "claim" insert --1--;
Col. 8, line 25, change "pints" to --points--; and
        line 48, after "gingival" insert --portion--.
```

Signed and Sealed this

Eleventh Day of January 1977

[SEAL]

Attest:

RUTH C. MASON
*Attesting Officer*

C. MARSHALL DANN
*Commissioner of Patents and Trademarks*